US012702632B2

(12) United States Patent
Clarsund

(10) Patent No.: US 12,702,632 B2
(45) Date of Patent: Aug. 11, 2026

(54) PROTEASE FORMULATION FOR TREATMENT OF MICROBIAL INFECTIONS

(71) Applicant: ZYMIQ Technology AB, Lund (SE)

(72) Inventor: Mats Clarsund, Saxtorp (SE)

(73) Assignee: ZYMIQ TECHNOLOGY AB, Lund (SE)

( * ) Notice: Subject to any disclaimer, the term of this patent is extended or adjusted under 35 U.S.C. 154(b) by 480 days.

(21) Appl. No.: 17/998,059

(22) PCT Filed: May 12, 2021

(86) PCT No.: PCT/EP2021/062630

§ 371 (c)(1),
(2) Date: Nov. 7, 2022

(87) PCT Pub. No.: WO2021/228942

PCT Pub. Date: Nov. 18, 2021

(65) Prior Publication Data

US 2023/0165776 A1 Jun. 1, 2023

(30) Foreign Application Priority Data

May 13, 2020 (EP) .................................... 20174324

(51) Int. Cl.

| | |
|---|---|
| ***A61K 8/66*** | (2006.01) |
| ***A61K 8/19*** | (2006.01) |
| ***A61K 8/34*** | (2006.01) |
| ***A61K 8/73*** | (2006.01) |
| ***A61K 9/00*** | (2006.01) |
| ***A61K 47/02*** | (2006.01) |
| ***A61K 47/10*** | (2017.01) |
| ***A61K 47/36*** | (2006.01) |
| ***A61P 17/00*** | (2006.01) |
| ***A61P 31/04*** | (2006.01) |
| ***A61Q 17/00*** | (2006.01) |

(52) U.S. Cl.

CPC .................. *A61K 8/66* (2013.01); *A61K 8/19* (2013.01); *A61K 8/345* (2013.01); *A61K 8/735* (2013.01); *A61K 9/0014* (2013.01); *A61K 9/0063* (2013.01); *A61K 47/02* (2013.01); *A61K 47/10* (2013.01); *A61K 47/36* (2013.01); *A61P 17/00* (2018.01); *A61P 31/04* (2018.01); *A61Q 17/005* (2013.01)

(58) Field of Classification Search

None

See application file for complete search history.

(56) References Cited

U.S. PATENT DOCUMENTS

| | | | | |
|---|---|---|---|---|
| 3,560,392 A | | 2/1971 | Eymery et al. | |
| 5,980,925 A | * | 11/1999 | Jampani .................. | A61K 8/43 424/404 |
| 2013/0296262 A1 | * | 11/2013 | Brown ................. | A61K 31/728 514/54 |
| 2017/0107503 A1 | * | 4/2017 | Clarsund ................. | A61P 17/02 |
| 2018/0007909 A1 | * | 1/2018 | Daigle .................. | A61K 47/12 |

FOREIGN PATENT DOCUMENTS

| | | | | |
|---|---|---|---|---|
| DE | 19649098 A1 | * | 5/1998 | ............ A61K 38/48 |
| JP | H034790 A | | 1/1991 | |
| JP | H11164699 A | | 6/1999 | |
| JP | H11279079 A | | 10/1999 | |
| JP | 2017505624 A | | 2/2017 | |
| WO | 2015/114343 A1 | | 8/2015 | |
| WO | 2017/017027 A1 | | 2/2017 | |
| WO | WO-2018138292 A1 | * | 8/2018 | |

OTHER PUBLICATIONS

Asadi, A. et al., A review on anti-adhesion therapies of bacterial diseases, Infection, 47: 13-23, 2019.

Bryers, J. Medical Biofilms, Biotechnology and Bioengineering, 100(1), May 1, 2008.

Buckland, E. et al., Characterisation of antimicrobial usage in cats and dogs attending UK primary-care companion animal veterinary practices, Veterinary Record, Aug. 19, 2016.

Craik, C. et al., Proteases as therapeutics, Biochem J., 435(1): 1-16, Apr. 1, 2011.

Gilbert, P. et al., Biofilm Susceptibility to Antimicrobials, Advances in Dental Research, 11(1): 160-167, Apr. 1997.

Meena, H. et al., A Review on Microbial Pathogenesis and Host Response, Model Organisms for Microbial Pathogenesis, Biofilm Formation and Antimicrobial Drug Discovery, Springer, Singapore, pp. 47-60, 2020.

Rosenthal, M. et al., Skin microbiota: Microbial community structure and its potential association with health and disease, Infect Genet Evol., 11(5): 839-848, Jul. 2011.

Schommer, N. et al., Structure and function of the human skin microbiome, Trends Microbiol., 21(12): 660-668, Dec. 2013.

Shaw, L. et al., Modelling microbiome recovery after antibiotics using a stability landscape framework, The ISME Journal, 13:1845-1856, 2019.

(Author unknown) New report calls for urgent action to avert antimicrobial resistance crisis, World Health Organization, Apr. 29, 2019.

Clarsund, M. et al., A Randomized, Double-Blind, Placebo-Controlled Pilot Clinical Study on ColdZyme® Mouth Spray against Rhinovirus-Induced Common Cold, Open Journal of Respiratory Diseases, 7: 125-135, 2017.

* cited by examiner

*Primary Examiner* — Sahana S Kaup

*Assistant Examiner* — Ashlee E Wertz

(74) *Attorney, Agent, or Firm* — Weston R. Gould; DINSMORE & SHOHL LLP

(57) ABSTRACT

The present invention relates to a stable protease formulation. Furthermore, it relates to a stable protease formulation for use in medicine and cosmetics, as well as a method of preventing and reducing biofilm formulation.

20 Claims, 10 Drawing Sheets

A

B

PROTEASE FORMULATION FOR TREATMENT OF MICROBIAL INFECTIONS

CROSS REFERENCE TO RELATED APPLICATIONS

This application is a U.S. National Stage of international application PCT/EP2021/062630 filed May 12, 2021, which claims priority to European Application No: 20714324.2 filed May 13, 2020, the entire contents of each of which are incorporated herein by reference.

TECHNICAL FIELD

The present invention relates to a stable protease formulation for the treatment of microbial infections.

BACKGROUND

Bacterial, fungus, and viral infections can be non-hostile relatively mild short-term infections to aggressive life-threatening infections. Microbial adhesion on the host cell membrane is the most common mode of establishing an infection in the host. Microbial surface protein recognizes cell surface protein that initiates microbial infection via adhesion, internalization, colonization, and secretion of toxic molecules enabling bacterial cell development and growth within the host tissue (Meena et al. 2020). A good strategy to treat and prevent microbial infections could be to reduce or prevent the first step in infection, microbial adhesion.

Surfaces of mammalian bodies that are exposed to the external environment are colonized by microbes, the microbiota. Some of the endogenous microbes can, under certain circumstances, cause disease as well as some of the exogenous pathogens that live in the external environment, or on other animals, can overcome our antimicrobial defences and do us harm if we come into contact with them. A good strategy to convert a pathogenic dysbiotic microbiota to a healthy symbiotic microbiota could be to target biofilm structures and the adhesion mechanism to reduce overgrowth of pathogens and to increase microbial diversity. Several studies have identified differences in the microbes present in diseased skin versus those present in healthy skin (Rosenthal et al. 2011) and indicates that an imbalance of microorganisms, termed dysbiosis, exists in numerous pathologies.

The traditional approach for elimination of skin infection in animals has been to attempt to target the offending agent with non-specific antimicrobials such as chlorhexidine. As more information is obtained about the commensal skin microbiome, questions should be raised about whether such a nonspecific approach is ideal (Rosenthal et al). It is likely that e.g. chlorhexidine that are commonly used in the treatment of pyoderma have efficacy against much of the core microbiome and therefore may suppress both pathogenic and beneficial components.

The unrestrained use of antibiotics has led to increasing antibiotic resistance, one of the most urgent health risks of our time, leading to an emerging rise of non-treatable human infections (WHO, 2019). Antibiotics are also commonly found in veterinary treatment of animals, where many of the drugs used are the same ones used in the treatment of bacterial infections in humans, and antibiotic resistance are associated with treatment failures and subsequent poor animal health. Companion animals are also able to acquire and exchange multidrug resistant pathogens with humans, and may serve as a reservoir of antimicrobial resistance for in-contact people (Buckland et al, 2016).

It has become increasingly important to develop new antimicrobials capable of withstanding the repertoire of bacterial resistance mechanisms. Targeting bacterial virulence properties such as adhesion and colonisation instead of viability is considered a valuable alternative strategy to antibiotic therapy (Asadi et al, 2019). Adhesion of the pathogen to host cells or tissue is the first step during bacterial infection and is also the first step to generate colonisation (biofilms). Biofilm-producing bacteria are believed to account for up to 80 percent of all bacterial infections (Bryers, 2008). Biofilms are communities of microorganisms protected by a self-synthesised layer of complex polysaccharides, proteins, lipids, and extracellular DNA. When bacteria act as biofilm, their resistance to both immune system and antibiotics can be increased by up to 1000 times (Gilbert et al, 1997). An anti-adhesion therapy would also be less likely to result in the emergence of mutations leading to resistance, due to reduced impact on the level of selective pressure on the bacterial population.

Antibiotics are commonly employed systemically to inhibit the growth of pathogenic bacteria and will during treatment act on a range of bacterial species in our commensal microbiota, which is of importance for our health. This can lead to a reorganisation of resident communities, including decreased bacterial diversity and outgrowth by previously minor contributors in gut and skin microbial populations. The human skin and mucosa, for example, is a complex barrier organ made of a symbiotic relationship between microbial communities in constant dialogue with the host's innate and adaptive immune system, a well-controlled but delicate equilibrium, mandatory for a healthy skin. Antibiotic-induced alterations of healthy microbiota can persist for several months or years post-treatment (Shaw et al, 2019).

Enzymes, and particularly proteases, are very suitable to reduce or inhibit microbial adhesion, such as bacterial adhesion, and to dissolve the biofilm without killing microbials. Proteases have been used in medicine for several decades and is an established and well-tolerated class of therapeutic agents (Craik et al, 2011).

There is an urgent need to develop new highly stable topical antimicrobial compositions, such as antibacterial compositions, that target microbial/bacterial adhesion, which is based on non-toxic compounds, that do not induce resistance and that has no or low impact on patients' natural microbiota.

SUMMARY

The inventors of the present invention have developed a novel formulation. Said formulation is a stable protease formulation capable of preventing and reducing biofilm formation as well as to increase microbial diversity in/on a subject or biological surface. Furthermore, said formulation does not induce microbial resistance and can therefore be used instead of antibiotics. Thus, the formulation described herein carry high potential for clinical use and provides a solution to the challenge of reducing the use of antibiotics.

Therefore, in one aspect, the disclosure relates to a composition comprising:

i. 0.01 to 0.2% w/w protease;

ii. 50 to 70% w/w glycerol;

iii. 0.0 to 0.1% w/w hyaluronic acid; and iv. 0.01 to 0.2% w/w salt comprising a divalent cation.

In another aspect, the disclosure relates to said composition for use in medicine.

In yet another aspect, the disclosure relates to a composition comprising i. a protease;
ii. glycerol;
iii. hyaluronic acid; and
iv. a divalent cation, for use in the treatment of conditions selected from the group consisting of microbial infections, dermatological conditions and oral conditions, in and/or on a mammal.

In one aspect, the disclosure relates to a composition comprising i. a protease;
ii. glycerol;
iii. hyaluronic acid; and
iv. calcium dichloride, for cosmetic use, in and/or on a mammal.

In another aspect, the disclosure relates to a method for prevention and/or reduction of biofilm, wherein the method comprises administration of a composition according to any one of the preceding claims.

In yet another aspect, the disclosure relates to a method for increasing microbial diversity, wherein the method comprises administration of the said composition.

In one aspect, the disclosure relates to a method of manufacturing the composition described herein above, comprising mixing the components at 25° C., in the following order:

i. glycerol
ii. buffer;
iii. hyaluronic acid; and
iv. protease.

DETAILED DESCRIPTION

Definitions

Figure 1:
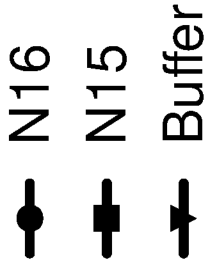
FIG. 1. Formulation optimisation increases the stability of trypsin in solution. Plots displaying the effect of various formulations on the remaining activity of trypsin after storage at (40±2° C./100% RH). Formulation composition (N16) contains glycerol 60 w/w %, $CaCl_2$) 0.1 w/w %, Collagen 0.3 w/w % and 0.04 w/w % trypsin at pH 8.5. Formulation composition (N15) contains glycerol 50 w/w %, $CaCl_2$) 0.1 w/w %, Collagen 0 w/w % and 0.04 w/w % trypsin at pH 8.5. The (Buffer) solution contained 0.04 w/w % trypsin at pH 7.5. Non-linear regression was used to estimate half-life.
Figure 1:
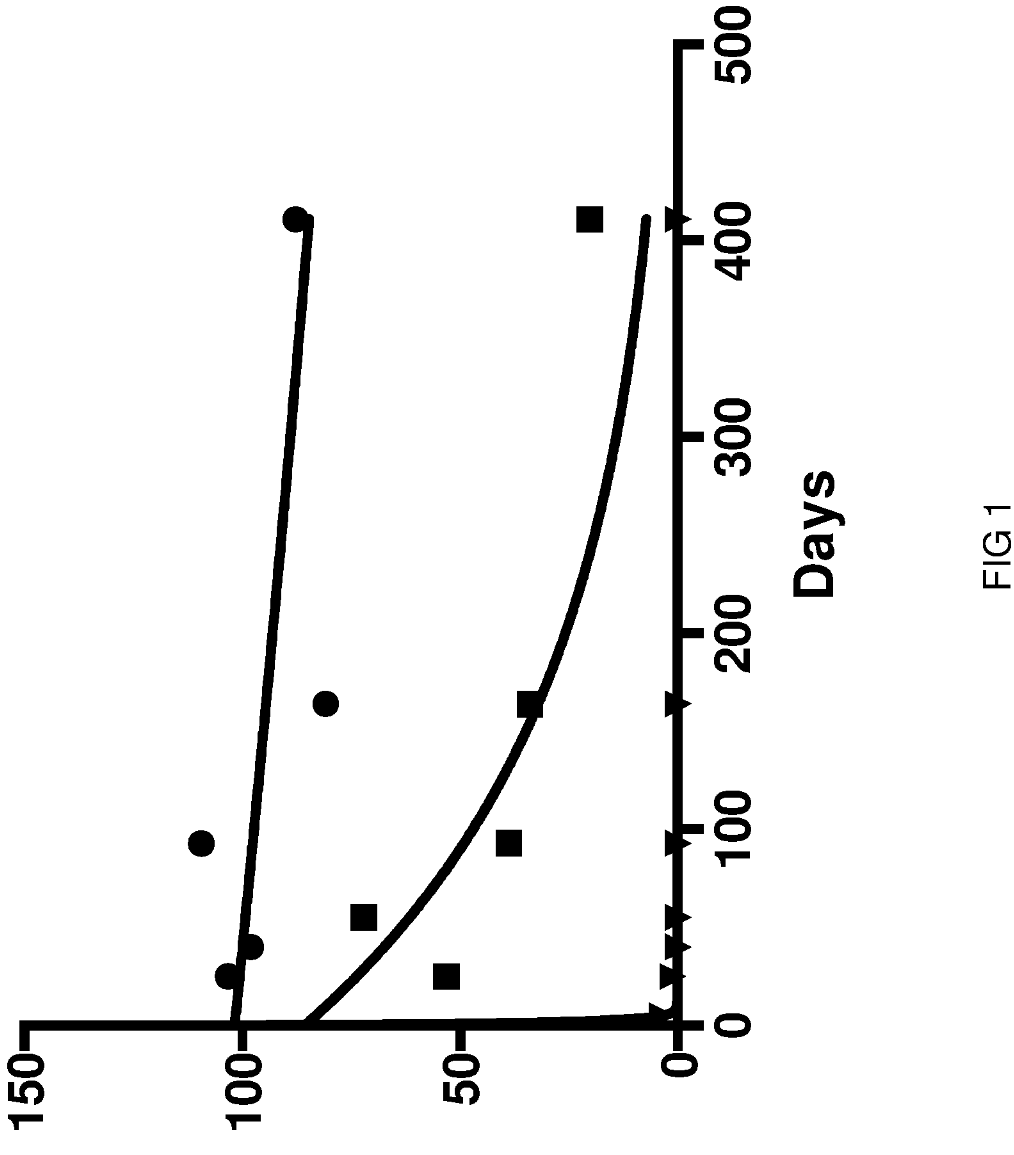

The term "protease" as used herein means an enzyme that cleaves a polypeptide of any length, short or long, at a peptide bond, for example by hydrolysing the peptide bond. The substrate of a protease is thus a polypeptide. The substrate can be a naturally occurring polypeptide or a synthetic polypeptide.

The term "biofilm" denotes an extracellular matrix in which microorganisms are dispersed and/or form colonies. The biofilm typically is made of polysaccharides and other macromolecules. In addition, in the present disclosure, the phrases "preventing a biofilm" "reducing a biofilm", or "decreasing a biofilm", and like phrases, means the prevention of biofilm growth, reduction in the rate of biofilm growth, partial eradication of existing biofilm, and/or complete eradication of existing biofilm.

The term "stability" as used herein refers to in vivo stability and storage stability (e.g., storage stability at room temperature).

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The term "microbial infection" refers to the undesired proliferation or presence of invasion of pathogenic microbes in a host organism. This includes the excessive growth of microbes that are normally present in or on the body of a mammal or other organism. More generally, a microbial infection can be any situation in which the presence of a microbial population(s) is damaging to a host mammal. Thus, a microbial infection exists when excessive numbers of a microbial population are present in or on a mammal's body, or when the effects of the presence of a microbial population(s) is damaging the cells or other tissue of a mammal.

The term "microbial diversity" as used herein refers to a measure of how many different types of microbial species there are in a within a particular environment, such as the mouth or on the skin of a mammal, while at the same time taking into account the overall representation of the species relative to other species.

In the context of the present disclosure, the term "w/w" means a "weight/weight". The expression "% w/w" is synonymous to "wt %" or "weight-percent". By way of example, 10 g of a composition comprising 50% w/w of A comprises 5 g A.

In the context of the present disclosure, phrases such as "a composition comprising X to Y % of A" are taken to mean a composition comprising A in the range of X to Y %, both thresholds included. That is, the composition does not comprise less than X % of A, and the composition does not comprise more than Y % of A, provided X is smaller than Y.

Stable Formulation

The present disclosure relates to a stable protease formulation for treatment of microbial infections. Proteases are very suitable in treatments against microbial infections, biofilm, and are non-toxic and well-tolerated as a therapeutic agent. It is also an advantage with a formulation that do not induce resistance and that can be used instead of antibiotics.

Therefore, in one embodiment, the disclosure relates to a composition comprising:

i. 0.01 to 0.2% w/w protease;
ii. 50 to 70% w/w glycerol;
iii. 0.0 to 0.1% w/w hyaluronic acid; and
iv. 0.01 to 0.2% w/w salt comprising a divalent cation.

In one embodiment of the present disclosure, the divalent cation of said composition is calcium. In a specific embodiment of the present disclosure, the composition comprises 0.01 to 0.2% of a calcium salt. In a specific embodiment of the present disclosure, the composition comprises 0.01 to 0.2% calcium chloride.

In another embodiment, the composition further comprises 0.1 to 0.4% w/w buffer, e.g. a pH buffer. In one embodiment of the present disclosure, the buffer may be a mixture of two or more buffer systems.

In yet another embodiment, the buffer of said composition is selected from the group consisting of Tris (2-Amino-2-(hydroxymethyl)propane-1,3-diol) and MOPS (3-Morpholinopropane-1-sulfonic acid). A person skilled in the art will appreciate the use of other pharmaceutically acceptable buffers.

In one embodiment, the composition further comprises a monosaccharide. For example, the monosaccharide may be a pentose or a hexose. The monosaccharide may be present in its cyclic form, in its linear form, or as a mixture of both forms. In one embodiment of the present disclosure, the composition comprises 0.0 to 0.2% w/w monosaccharide, such as 0.01 to 0.2% w/w monosaccharide. For dermal application, e.g. for the application of a gel, the composition may advantageously comprise a monosaccharide. Thus, in one embodiment, the composition is a dermal composition and comprises a monosaccharide, such as 0.01 to 0.2% w/w monosaccharide. In another embodiment, the composition comprises essentially no monosaccharide, such as 0.0% w/w monosaccharide. In another embodiment, the monosaccharide of said composition is mannose. In a specific embodiment of the disclosure, the composition comprises 0.0 to 0.2% w/w mannose, such as 0.01 to 0.2% w/w mannose.

In one embodiment of the disclosure, the composition further comprises collagen. The collagen may be any collagen extracted and purified from tissues of animals and fishes and shellfishes. The extraction and decomposition method or the modification degree of the resulting collagen is not specifically limited. In a specific embodiment of the present disclosure, the collagen may be modified, such as chemically modified. In a specific embodiment, the collagen is gelatin. In one embodiment of the disclosure, the composition comprises 0.0 to 0.3% w/w collagen, such as 0.01 to 0.3% w/w collagen. For cosmetic use, the formulation may advantageously comprise collagen. Collagen may improve stability of dermal compositions, and may have further advantageous properties for dermal use. Thus, in one embodiment of the disclosure, the composition comprises collagen, such as 0.01 to 0.3% collagen. In another embodiment of the disclosure, the composition comprises essentially no collagen, such as 0.0% w/w collagen.

In one embodiment, the protease of said composition is trypsin. Trypsin is a serine protease which predominantly cleaves peptide chains at the carboxyl side of the amino acids lysine and arginine. In one embodiment of the disclosure, the composition comprises 0.01 to 0.2% w/w protease, such as 0.01 to 0.2% w/w trypsin. In a further embodiment of the disclosure, the composition comprises 0.02 to 0.09% w/w protease, such as 0.02 to 0.09 w/w trypsin. In a specific embodiment of the disclosure, the composition comprises essentially 0.04% w/w protease, such as 0.04% w/w protease.

In one embodiment of the disclosure, the composition comprises one or more of a diol, a triol, or a polyol, such as glycerol, propylene glycol, or a sugar alcohol. In one embodiment, the composition comprises a diol. In a specific embodiment, the composition of the disclosure comprises 50 to 80% w/w of the diol, such as 50 to 75% w/w, such as 50 to 70% w/w, such as 50 to 62% w/w. In a specific embodiment, the composition comprises 50 to 80% w/w glycerol, such as 50 to 75% w/w, such as 50 to 70% w/w, such as 50 to 62% w/w. In another specific embodiment of the disclosure, the composition comprises essentially 60% diol, such as glycerol. The role of the diol, triol, and/or polyol is in part to reduce the water activity in the composition. Reducing the water activity in turn deactivates the protease. Deactivation of the protease improves its stability in the composition.

In one embodiment of the disclosure, the composition comprises a glycosaminoglycan, such as hyaluronic acid. As used herein "hyaluronic acid" encompasses hyaluronic acid and its hyaluronate salts, including, but not limited to, sodium hyaluronate, potassium hyaluronate, magnesium hyaluronate and calcium hyaluronate. In a specific embodiment, the composition comprises 0.0 to 0.1% w/w glycosaminoglycan, such as hyaluronic acid. In another specific embodiment, the composition comprises 0.002 to 0.1% w/w glycosaminoglycan, such as hyaluronic acid. In another specific embodiment, the composition comprises 0.0 to 0.04% w/w glycosaminoglycan, such as hyaluronic acid. In another specific embodiment, the composition comprises 0.002 to 0.04% w/w glycosaminoglycan, such as hyaluronic acid. In another specific embodiment, the composition comprises essentially 0.02% w/w glycosaminoglycan, such as hyaluronic acid. In one embodiment of the present disclosure, the composition comprises 0.0 to 0.1% w/w hyaluronic acid, such as 0.002 to 0.1% w/w.

In another embodiment of the disclosure, the composition comprises or consists essentially of:

i. 0.02 to 0.09% w/w protease;
ii. 50 to 62% w/w glycerol;
iii. 0.0 to 0.04% w/w hyaluronic acid;
iv. 0.01 to 0.1% w/w $CaCl_2$);
v. 0.1 to 0.4% w/w Tris or MOPS;
vi. 0.0 to 0.2% w/w mannose; and
vii. 0.0 to 0.3% w/w collagen.

In another embodiment of the disclosure, said composition comprises or consists essentially of:

i. 0.04% w/w protease;
ii. 60% w/w glycerol;
iii. 0.2% w/w hyaluronic acid;
iv. 0.01% w/w calcium dichloride; and
v. 0.1% w/w Tris or MOPS.

In another embodiment of the disclosure, said composition comprises or consists essentially of:

i. 0.04% w/w protease;
ii. 60% w/w glycerol;
iii. 0.02% w/w hyaluronic acid;
iv. 0.01% w/w calcium dichloride; and
v. 0.1% w/w Tris or MOPS.

In yet another embodiment of the present disclosure, the combination of components of said composition does not exceed 100%.

In another embodiment, the pH of said composition is between 6.0 to 7.5, such as 6.2 to 7.4. pH of solutions can be assessed in a number of ways. For example, pH can be assessed using a pH electrode or a pH indicator.

In one embodiment, the composition further comprises water. In a specific embodiment of the disclosure, at least part of the water of the composition originates from the buffer. The presence of free water can activate and/or destabilize the protease. Water in the composition may be deactivated by other components, such as for instance glycerol and other alcohols describes herein. Accordingly, in one embodiment, the composition comprises less than 50% w/w water, such as 20 to 50% w/w water. To improve the stability of the protease, it is important that the water activity in the composition is low. Upon applying the composition to e.g. a wound, the skin, or in the oral cavity, water from said wound, skin, or oral cavity mixes with the composition, increasing the water activity. This in turn activates the protease.

In another embodiment, the composition is the form of a spray, a gel, a cream, lotion, an ointment, a foam, or a dental chew.

In one embodiment, the disclosure relates to said composition for use in medicine. Specifically, one embodiment provides for the disclosed composition for use in medicine.

In another embodiment, the disclosure provides a composition comprising i. a protease;
ii. glycerol;
iii. hyaluronic acid; and
iv. a divalent cation, for use in the treatment of conditions selected from the group consisting of microbial infections, dermatological conditions and oral conditions, or for cosmetic use, in and/or on a mammal.

In one embodiment, the disclosure provides a composition comprising i. a protease;
ii. glycerol;
iii. hyaluronic acid; and
iv. a divalent cation, for use in the treatment of a condition selected from the group consisting of microbial infections, dermatological conditions and oral conditions, in a mammal.

In one embodiment of the present disclosure, the microbial infection is selected from the group consisting of bacterial infections, fungal infections, yeast infections and viral infections.

In another embodiment, the dermatological condition is a skin infection. In yet another embodiment, the dermatological condition is an inflammatory skin disease. In another embodiment, the inflammatory skin disease is selected from the group consisting of atopic dermatitis, psoriasis, rosacea and acne.

In one embodiment, the oral condition is an oral infection. In one embodiment, the oral condition is a dental infection. In another embodiment, the mammal is a dog, a cat, a horse or a human.

In one embodiment, the protease of said composition is trypsin.

In one embodiment of this invention, the divalent cation of said composition is calcium.

In another embodiment, the composition further comprises 0.1 to 0.4% w/w buffer.

In yet another embodiment, the buffer of said composition buffer is selected from the group consisting of Tris and MOPS.

In one embodiment, the composition further comprises a monosaccharide.

In another embodiment, the monosaccharide of said composition is mannose.

In one embodiment of this invention, the composition further comprises collagen.

In another embodiment, the pH of said composition is between 6.0 to 7.5, such as 6.2 to 7.4.

In one embodiment, the composition further comprises water.

In another embodiment, the composition is the form of a spray, a gel, a cream, lotion, an ointment, a foam, or a dental chew.

In one embodiment of the present disclosure, the composition is for topical use.

In another embodiment, the present disclosure relates to a method for prevention and/or reduction of biofilm, wherein the method comprises administration of a composition according to any one of the preceding claims.

In one embodiment, the biofilm is a biofilm in or on a mammal.

In another embodiment, the biofilm is a biofilm of a biological surface.

In one embodiment, the present disclosure relates to a method for increasing microbial diversity, wherein the method comprises administration of the said composition.

It is known in the art that the skin barrier and skin microbiota is essential for protection of the body against external aggressions, and that factors that alter the composition of skin microbiota and the skin barrier function inducing a state of dysbiosis (unbalanced state) which has been evidenced in some chronic inflammatory skin diseases such as atopic dermatitis, psoriasis, rosacea or acne (Schommer et al, 2013). Hence, compositions that stimulate the skin microbiome and microbial diversity could be a great use in the treatment of such conditions, and for cosmetic purposes.

Furthermore, the stable formulation of the present disclosure were found to have similar positive effect on reduction of clinically relevant pathogens as chlorhexidine. However, it is known in the art that chlorhexidine can cause allergic reactions (especially so in eczema patients), that cross-resistance to antibiotics have been reported and that it has limited effect against fungi and mycobacteria. Furthermore, chlorhexidine for dental use can cause side effects such as staining of teeth, increased calculus formation and negative effects on the oral (healthy) microbiome. Therefore, a person skilled in the art will appreciate that the use of the formulation of the present disclosure would be beneficial over chlorhexidine.

In another embodiment, the disclosure relates to a method of manufacturing the said composition comprising mixing the components at 25° C., in the following order:

i. glycerol
ii. buffer;
iii. hyaluronic acid; and
iv. protease.

One embodiment of the present disclosure provides for a method of treating a condition selected from the group consisting of microbial infections, dermatological conditions and oral conditions, in and/or on a mammal, said method comprising administering a composition comprising:

i. a protease;
ii. glycerol;
iii. hyaluronic acid; and
iv. a divalent cation, to a subject in need thereof.

EXAMPLES

Example 1: Stability Experiments

Methods

A fractional factorial design of 5 parameters, and their concentrations, was used to study the most important factors influencing trypsin stability (Table 1).

TABLE 1

The components that were tested when studying the stability of trypsin.

| Formulation Variable | Settings | Units |
|---|---|---|
| Glycerol | 50-62 | wt % |
| $CaCl_2$ | 0.01-0.1 | wt % |
| pH | 6-8.5 | pH |
| Enzyme | 0.02-0.09 | wt % |
| Collagen | 0-0.3 | wt % |

Various combinations were mixed and the pH was adjusted using MOPS buffer. Two different formulation were tested: Formulation composition N16 which contained glycerol 60 w/w %, $CaCl_2$) 0.1 w/w %, Collagen 0.3 w/w % and 0.04 w/w % trypsin at pH 8.5, and Formulation composition N15 containing glycerol 50 w/w %, $CaCl_2$) 0.1 w/w %, Collagen 0 w/w % and 0.04 w/w % trypsin at pH 8.5. A buffer solution was used as a control, containing 0.04 w/w % trypsin at pH 7.5. The test formulation, Formulation A, was also evaluated under same conditions.

The formulation mixes were put into sealed polypropylene bottles. Products from each formulation composition were placed on stability at a stressed condition (40±2° C./100% RH) for up to 411 days. Samples were pulled at predetermined time points and analysed directly by measuring the enzyme activity. The trypsin activity was measured at 30° C. using Z-Gly-Pro-Arg-pNA as substrate in a spectrophotometer at 405 nm. The decrease in absorbance per minute was used as activity parameter. The half-life or remaining activity relative to time point zero was determined and used to describe the stability. Non-linear regression was used to estimate half-life.

Results

The half-life for trypsin increased from 2 days in buffer to more than 400 days in the most stable formulations. The half-life could not be accurately determined in the most stable formulations since more than 88% of the enzyme activity still remained after 411 days. The remaining activity after storage at 40° C. for 411 days varied from 20 to 88% for the tested combinations (FIG. 1). Formulation A was also very stable with a remaining activity of >90% after storage at 40° C. for 119 days. Its shelf life at room temperature 25-30° C. was estimated to be more than 3 years.

Conclusion

It is possible to dramatically improve the stability of trypsin in solution at stressed conditions of 40° C. The expected shelf life at room temperature of optimised formulations is expected to be more than 3 years.

Example 2: Anti-Biofilm Activity

The aim of this study was to evaluate the test formulation, Formulation A, whose stability was tested in Example 1, against preformed biofilms as well as against biofilm formation using the MBEC™ Assay by following the ASTM E2799-12 standard. The ASTM E2799-12 is a standard test method for testing disinfectant efficacy against *Pseudomonas aeruginosa, Staphylococcus pseudintermedius* and *Malassezia pachydermatis* biofilm using the MBEC assay.

Methods

A mature biofilm was established on pegs under batch conditions with very low shear produced by gentle rotation of the device on an orbital shaker. At the end of 24-48 hours of growth, the pegs containing the biofilm were rinsed to remove planktonic cells and the peg lid was placed in a receiver plate. The wells in the receiver plate were filled according to an experimental design that contained the appropriate sterility, growth, and neutralizer controls as well as the disinfectants. In this study, the disinfectants were a formulation described in Table 2 and a negative control, which was a carrier solution with no active agent (Table 3). After a specified contact time, the peg lid was placed in a receiver plate containing neutralizer, and the entire device was placed in a sonicator to remove the biofilm and disaggregate the clumps. Samples from each well were then diluted, plated and the viable cells counted. The log reduction in viable cells was calculated by subtracting the mean log density for the treated biofilm from the mean log density for the untreated controls. The results were measured in colony-forming units (CFU)/peg.

TABLE 2

| Composition of Formulation A (w/w %) | |
|---|---|
| Component | Conc. (w/w %) |
| Glycerol | 60 |
| Tris | 0.1 |
| $CaCl_2 \times 2H_2O$ | 0.01 |
| Water | 39 |
| Hyaluronic acid | 0.02 |
| Trypsin | 0.04 |
| pH | 7.5 |

TABLE 3

Summary of experimental settings used in Example 2.

| Sample | Sample description | Contact time | Test dilutions % | Sample size |
|---|---|---|---|---|
| Formulation A | Test material | 4 hours for killing the biofilm | 33% of supplied stock solution | n = 6 |
| carrier solution (no active agent) | CAMHB - Negative Control | 4 hours for killing the biofilm | N/A | n = 6 |

CAMHB: Cation-adjusted Mueller-Hinton broth

Results

Figure 2A:
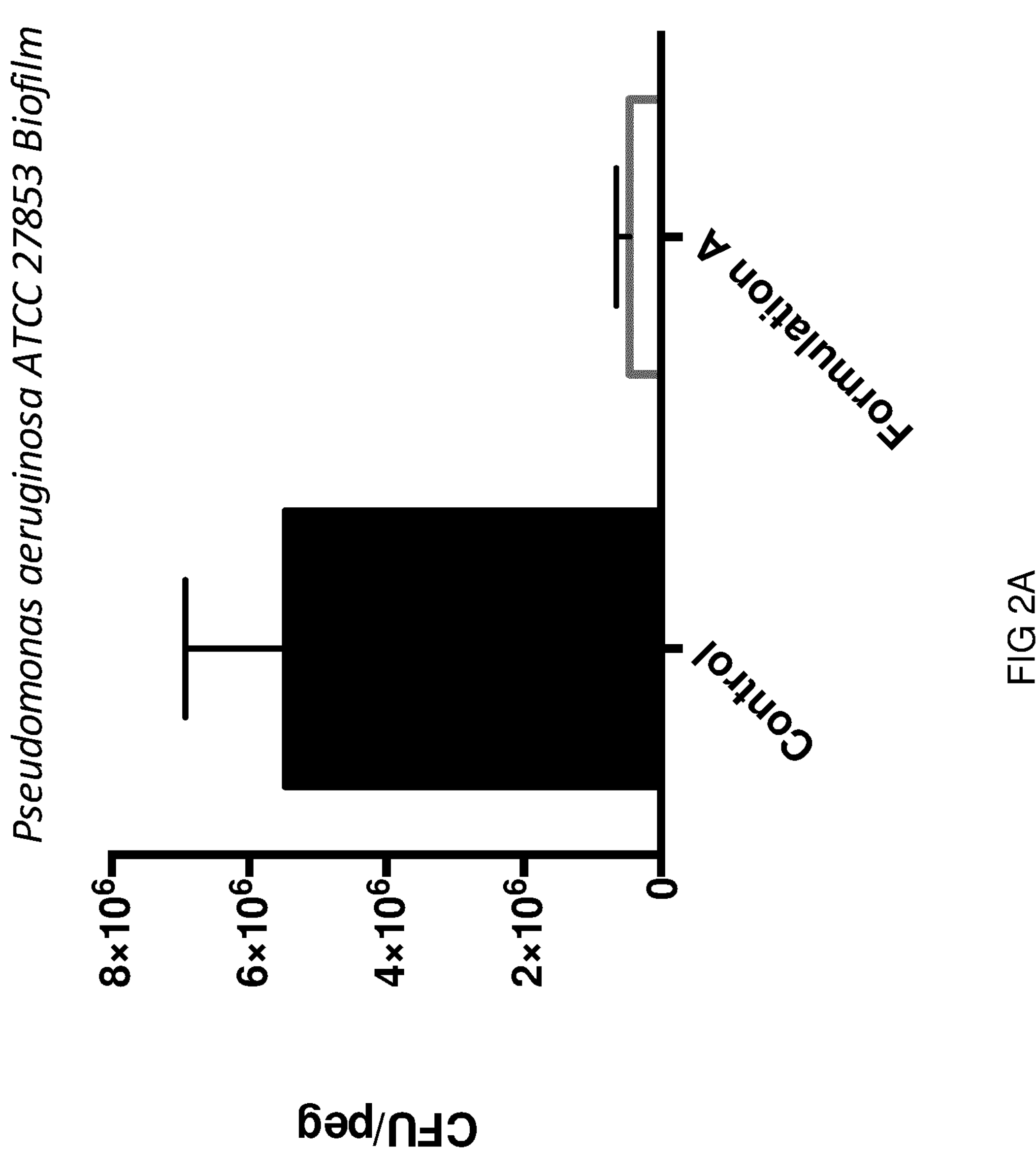
FIG. 2. Formulation A significantly decreases biofilm formation in vitro. Bar plots displaying the effect on preformed biofilms from (A) *Pseudomonas aeruginosa*, (B) *Staphylococcus pseudintermedius* and (C) *Malassezia pachydermatis* following treatment with a negative control formulation (n=12) and the test Formulation A (n=6). Formulation A significantly decreases the number of colony-forming units (CFU)/peg compared to the control formulation. Data is plotted as means with error bars (95% confidence intervals).
Figure 2B:
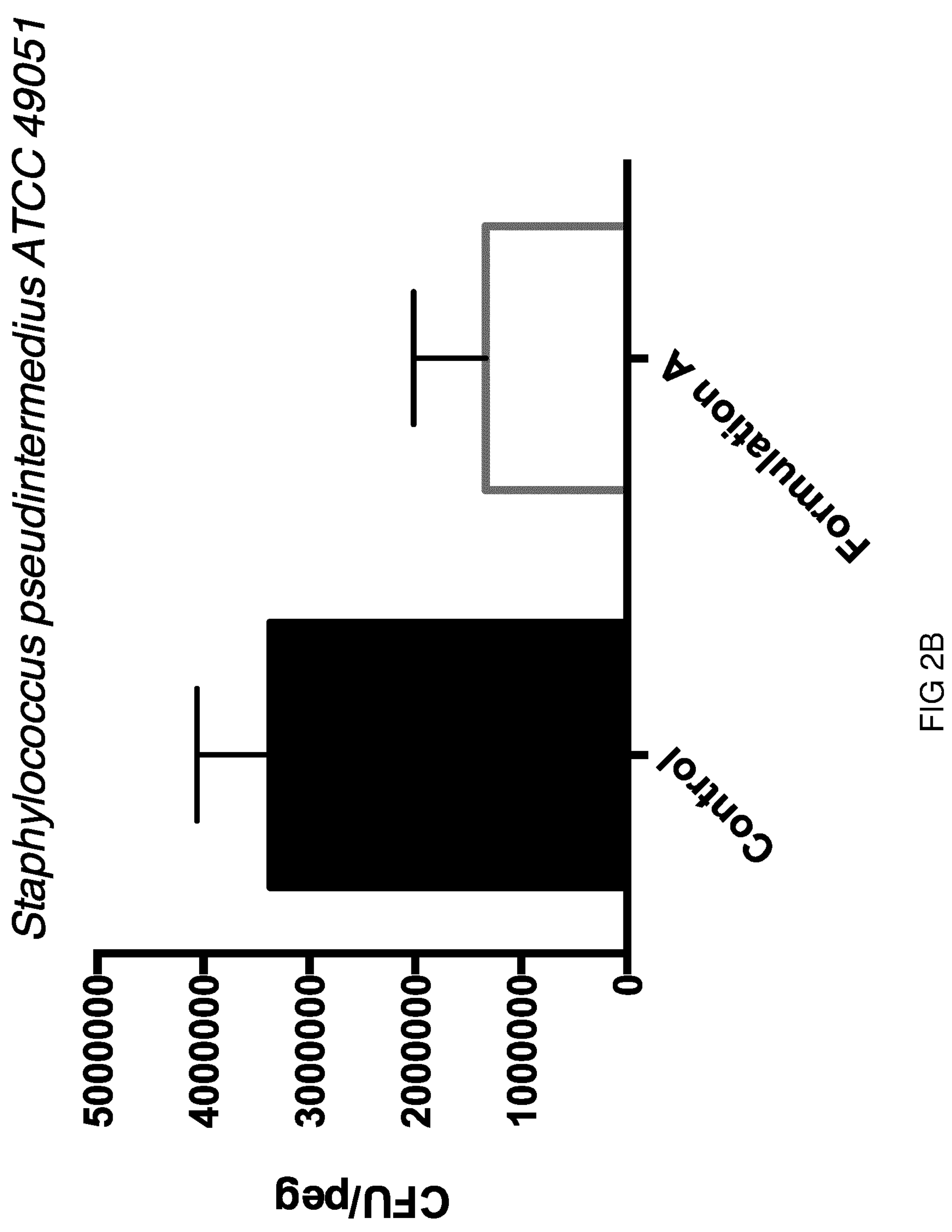
Figure 2C:
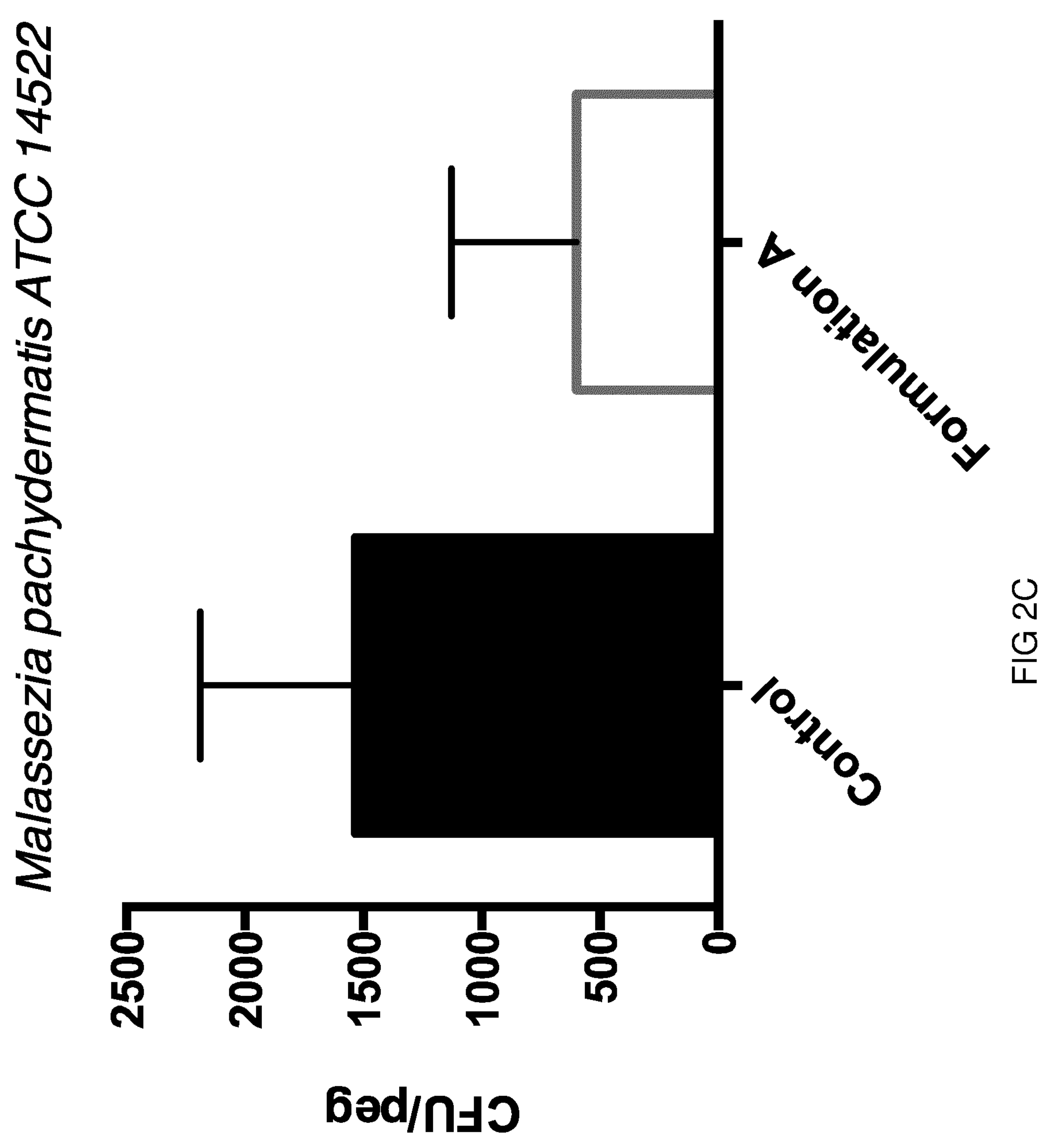

The number of CFU/peg were significantly decreased for all microbes analysed in the study; *Pseudomonas aeruginosa, Staphylococcus pseudintermedius* and *Malassezia pachydermatis*, after treatment Formulation A compared to the control formulation (FIG. 2).

Conclusion

Formulation A successfully decreased the biofilm formed by tested microbes.

Example 3: Microbial Diversity in the Nasal Folds of French Bulldogs (Clinical Study)

The aim of this clinical study was to compare two different solutions on the effect of the natural microbiota in skin folds of dogs.

Methods

The study was a randomized, single-blind and prospective study, including 19 privately owned dogs (French bulldogs). The two solutions tested were Formulation A (enzyme) with 0.002 w/w % denatonium benzoate added and a 2% chlorhexidine solution. Denatonium benzoate is a bittering agent, which was added to Formulation A to prevent dogs from licking on the wound or treated area. The included dogs were randomised into three different groups; one control group that did not receive any treatment (n=6) and two treatment groups; enzyme treatment group (n=7) and a chlorhexidine treatment group (n=6).

The following inclusion criteria were used:

i. Tentatively diagnosed with nasomaxillary fold dermatitis (intertrigo) based on history and clinical examination
ii. Lack of concurrent systemic illness or metabolic conditions, unless the condition is stable in the opinion of the primary investigator iii. Dog not pregnant or lactating
iv. Signed informed animal owner consent The following exclusion criteria were used:

i. Clinical lesions consistent with deep pyoderma in nasal folds (such as fistula, phlegmon and furuncle)
ii. Ulcerations in nose folds
iii. Dogs that did not allow being touched on the nose folds
iv. Any other form of topical treatment in the nose folds or any form of antibiotic treatment two weeks prior to or during the study period
v. Changes in ongoing treatment with oral corticosteroids from two weeks prior to the inclusion and throughout the study period
vi. Injections of corticosteroids from 90 days prior to inclusion and throughout the study period At day 0, the dog underwent general clinical examination. Cytology samples were taken from bilateral nasomaxillary folds. Swabs were collected from the dogs' nasomaxillary folds and sent for next generation DNA sequencing (MiDOG, CA, USA) according to manufacturer's instructions. On day 0, the pet owners were also informed of how to apply the test solution (enzyme treatment solution or chlorhexidine) on each nose fold twice daily (morning and evening) until the return visit to the clinic, except for the day of the visit. Two bottles of test product were provided to the owners, and they were instructed to store the test product at room temperature.

At day 14, the same tests and assessments as on day 0 were performed. Possible side effects were also noted at this visit. The pet owners were informed about continuing the treatment according to previous introductions another week and that treatment should not take place the day of the return visit and to return all spray bottles to the clinic at next visit.

At day 28, the same tests and assessments were performed as on previous visits to the clinic. Again, possible side effects were recorded. The weight of the test solution bottles is recorded. The pet owners were instructed to discontinue all topical product application and reassess patient in two weeks.

At day 42 (14 days after treatment was discontinued), the last collection of test samples and assessments were performed.

Results

Figure 3:
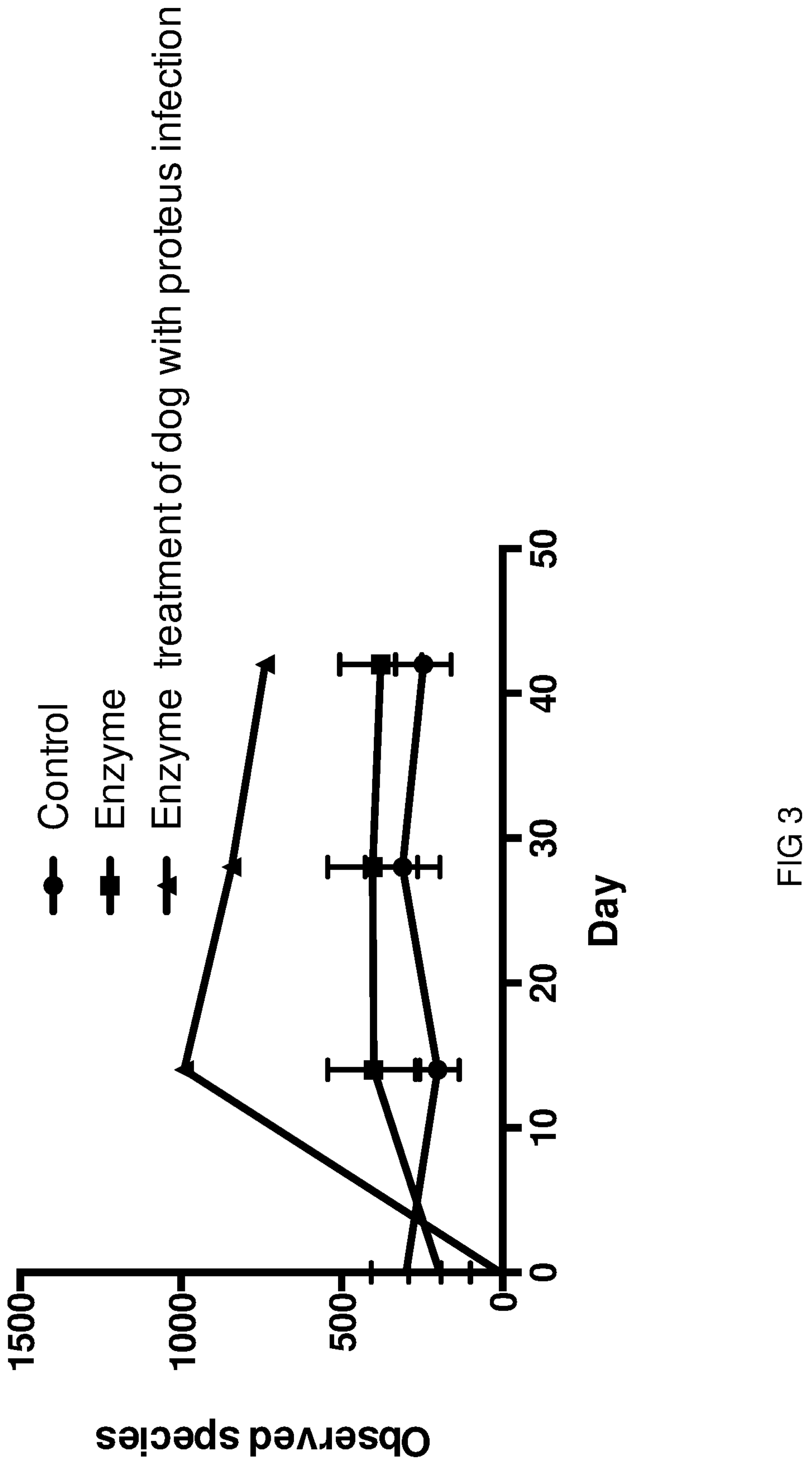
FIG. 3. The number of observed species increased after enzyme treatment. Plot displaying the number of species that were observed in the enzyme treated group (n=7) and in one of the dogs having a Proteus infection. The control group (n=6) did not receive any treatment at all. In the end of the study, the group with the largest number of observed species were the group treated with enzyme. No significant change in observed species could be seen in the control group. Data is plotted as means with error bars (standard error).
Figure 4:
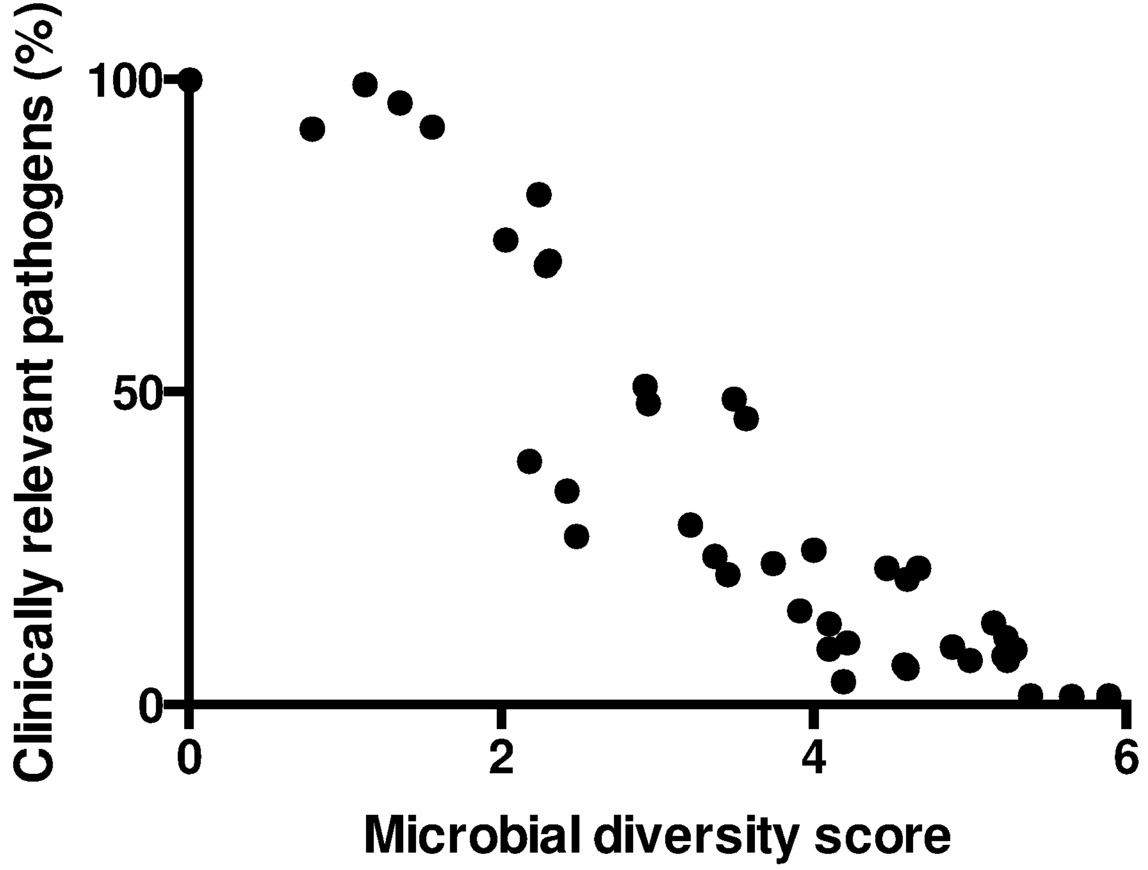
FIG. 4. There was a clear correlation between abundance of clinically relevant pathogens and microbial diversity. The abundance of clinically relevant pathogens were plotted against a microbial diversity score, the Shannon index, a quantitative measure that reflects how many different species there are in a dataset, which showed a clear correlation ($r^2$=0.8) between the two parameters. This indicates that a low abundance of clinically relevant pathogens is correlated with a high microbial diversity score.
Figure 5:
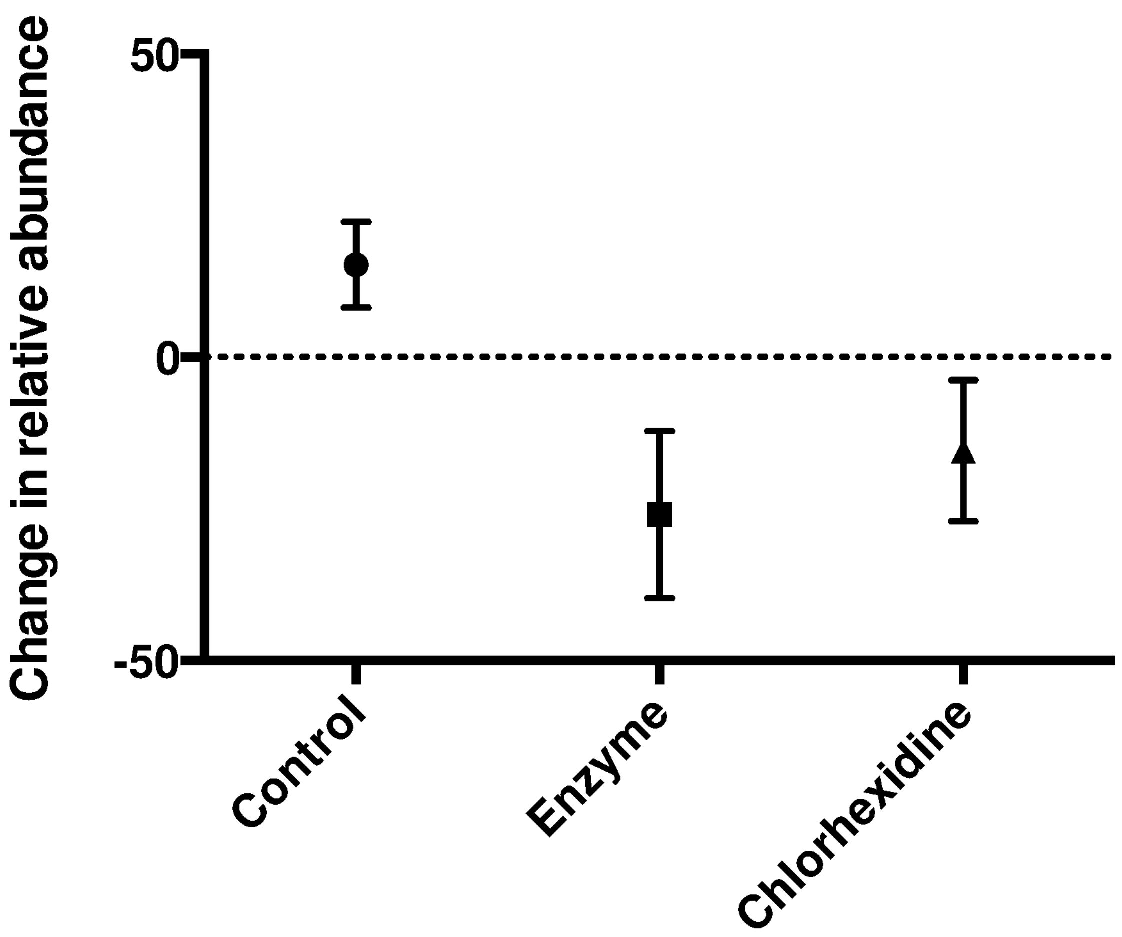
FIG. 5. The abundance of clinical relevant pathogens was significantly decreased in both treatment groups. Plot displaying the change in relative abundance of clinically relevant pathogens from day 0 to day 28 of the study period for all three patient groups. The control group displayed an increase of clinically relevant pathogens, while both treatment groups displayed a decrease. The group treated with enzyme displayed a slightly larger decrease (p=0.028) compared to the other treatment group, which received chlorhexidine treatment (p=0.048). Data is plotted as means with error bars (standard error).
Figure 6:
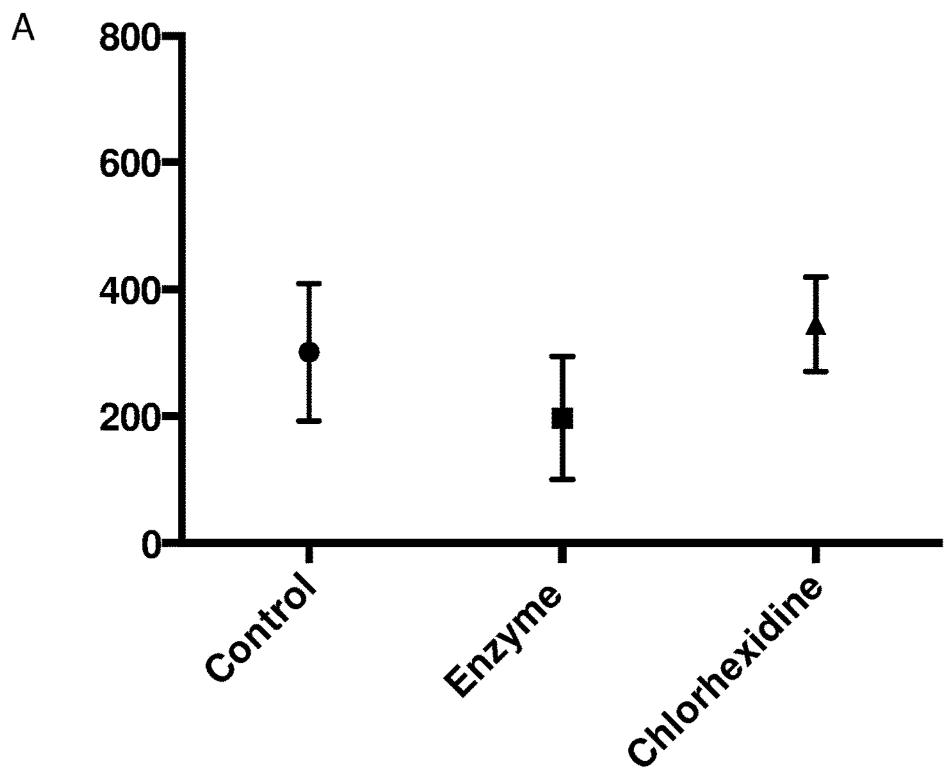
FIG. 6. The alpha diversity was primarily increased in the enzyme group. Plots displaying the alpha diversity, i.e. the average species diversity in the treated area, on (A) day 0 and (B) day 28. At day 28, the mean alpha diversity had increased from 197 to 404 (median; from 53 to 479) in the enzyme treatment group and for the chlorhexidine group a small non-significant increase from 359 to 392 (median; from 345 to 388) was observed. There was no apparent difference in the control group (mean; from 300 to 312, median; from 300 to 192). Data is plotted as means with error bars (standard error).
Figure 6:
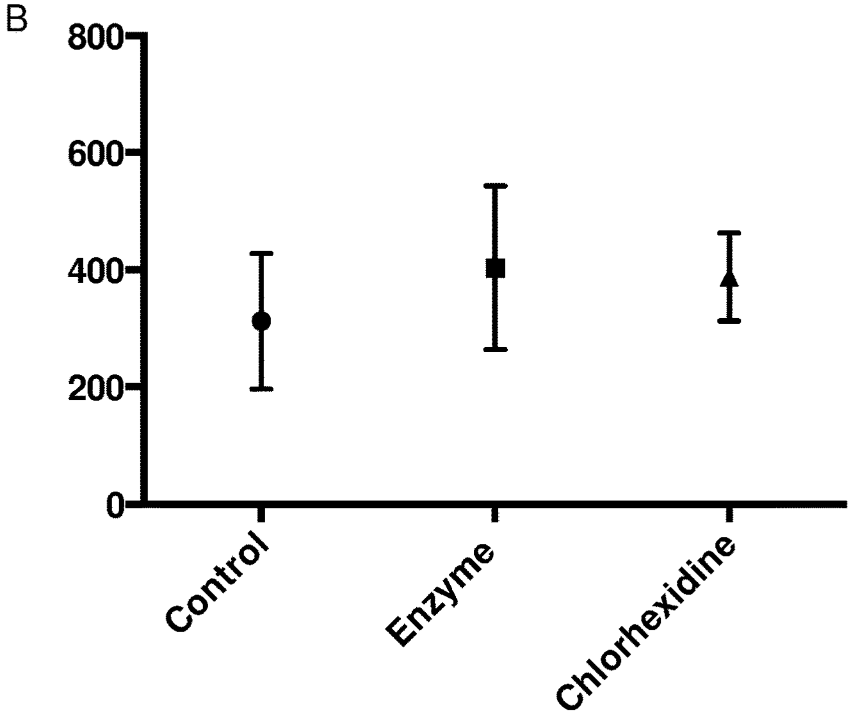

All dogs showed a low diversity at both bacterial and fungal phylum level, but high bacterial diversity and low fungal diversity at the species level. The main skin bacterial phyla inhabiting the skin fold of the 19 dogs were Firmicutes, Actinobacteria and Proteobacteria. The main skin fungal phyla were Ascomycota and Basidiomycota. The topical treatment increased the diversity of bacterial and fungal compositions over time, shown as an increase in microbial diversity score (FIG. 3). For the enzyme treatment group (Formulation A) the increase was 38%, for the chlorhexidine group 11% and for the control group it was <5%. A clear correlation ($r^2$=0.8) between abundance of clinically relevant pathogens and microbial diversity was seen, indicating that a low abundance of clinically relevant pathogens is correlated with a high microbial diversity score, the Shannon index, a quantitative measure that reflects how many different species there are in a dataset (FIG. 4). In both treatment groups the abundance of clinically relevant pathogens decreased significantly (enzyme treatment group; p=0.028, chlorhexidine group; p=0.048) compared to the control (FIG. 5). The alpha diversity, i.e. the average species diversity in the treated area increased primarily for the enzyme treatment group from day 0 (FIG. 6A) to day 28 (FIG. 6B).

Conclusion

Based on the results of this study, we conclude that topical therapy using Formulation A both reduces the relative abundance of clinically relevant pathogens and increases microbial diversity in the nasal folds of French bulldogs. This indicates that formulation A could be an alternative to chlorhexidine.

Example 4: Dental Health of Dogs (Clinical Study)

The aim of this study was to evaluate the treatment effect of Formulation A in order to improve the dental status of dogs.

Methods

This clinical study was an open label prospective study on 5 privately owned dogs. The following inclusion criteria were used:

i. An OraStrip® Dental Diagnostic test score (Gingivitis Score) 3 (meaning a risk of ≥97% of a moderate to severe active periodontal disease)

ii. Good to excellent health iii. Free of disease or infection iv. Recent dental>6-8 weeks ago v. Signed informed animal owner consent The OraStrip® Dental Diagnostic test (CET OraStrip, Virbac, Ft. Worth, TX) is a test to detect periodontal disease and to assess the risk of moderate to severe periodontal disease that can be performed at the clinic. The diagnostic test determines level of thiol, an organosulfur compound produced by the bacteria associated with periodontal disease and as a measure of level of gingivitis where 0 is no thiol detected (no gingivitis) and 1-5 indicates active and increasing gingivitis.

The following exclusion criteria were used in the study:

i. Multiple tooth extractions ii. Major dental procedures iii. Daily medication iv. Any other form of dental health treatment during the study period v. Non-compliance with the study protocol vi. Side effects of treatment, after recording of data. Possible side effects were handled by the physician At day 0, the dog underwent a relevant clinical examination at the clinic. The clinical examination included a dental status evaluation using the OraStrip® Dental Diagnostic test (on saliva) according to the manufacturer's instructions. A periodontal scoring was also performed in order to assess the degree of gingivitis and periodontitis (Table 4). Photos were taken of the dogs' teeth and gum. The pet owners were informed of how the Formulation A should be applied twice daily (morning and evening) until the return visit, and supplied with an instructions document. Each owner was supplied with one bottle of Formulation A, and informed that it should be stored at room temperature.

TABLE 4

Periodontal scoring of the dogs.

| PD Score/ Stage | Classification | Clinical manifestation |
|---|---|---|
| 0 | Clinically normal | No gingival inflammation or periodontitis clinically evident |
| 1 | Slight gingivitis | Gingivitis only without attachment loss. The height and architecture of the alveolar margin are normal |
| 2 | Early periodontitis | ≤25% of attachment loss at most. There is a stage 1 furcation involvement in multi-rooted teeth and early radiologic signs of periodontitis. The loss of periodontal attachment is less than 25%* |
| 3 | Moderate periodontitis | 25-50% of attachment loss*, or a stage 2 furcation involvement in multi-rooted teeth |
| 4 | Advanced periodontitis | ≥50% of attachment loss*, or a stage 3 furcation involvement in multi-rooted teeth |

*As measured either by probing of the clinical attachment level, or radiographic determination of the distance of the alveolar margin from the cemento-enamel junction relative to the length of the root At day 14, the periodontal grading and the OraStrip® Dental Diagnostic test were performed and recorded in the same way as at day 0. Again, a photo was taken of the dogs' teeth and gum, and the owner is informed about continuing the treatment according to previous instructions.

At day 28, the same tests and grading were performed as on previous visits. At this visit, possible side effects were also noted and the weight of the bottle was recorded.

Results

Figure 7:
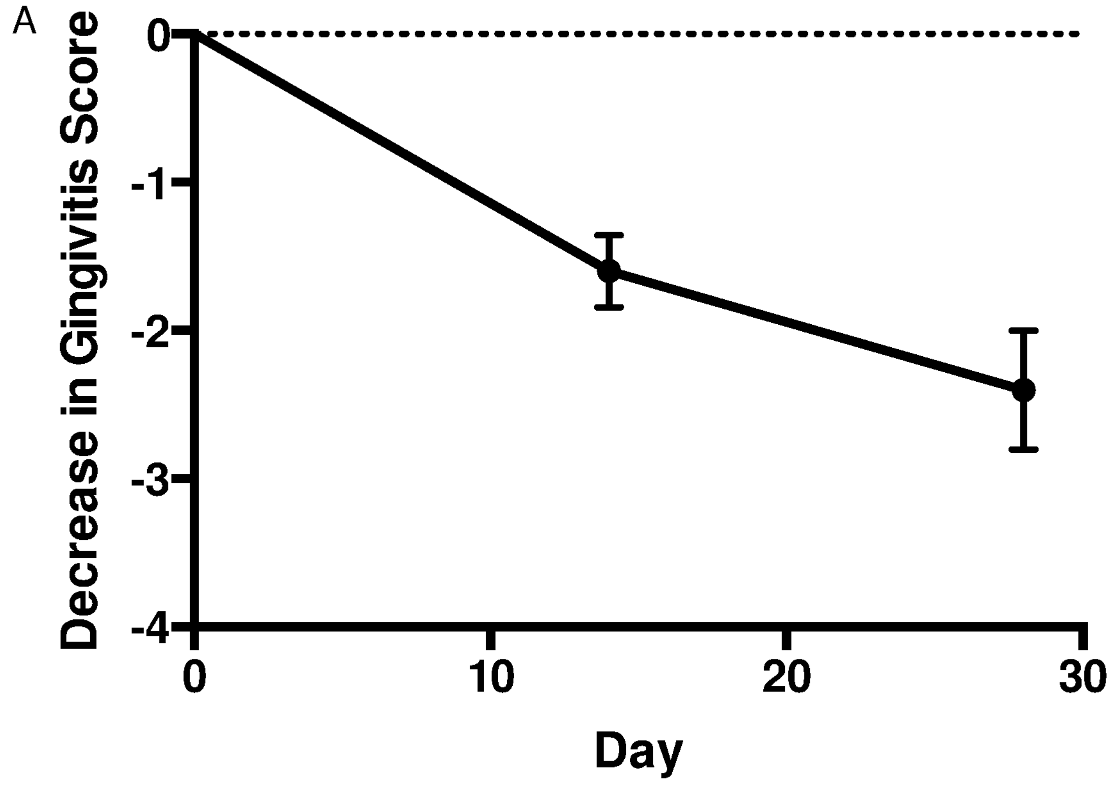
FIG. 7. The gingivitis score and periodontal score/grade was decreased in the treatment group (n=5). Plots displaying the decrease in (A) gingivitis score and (B) periodontal score after treatment with Formulation A. This suggests a decreased gingivitis and in general, an improved dental health among the dogs treated with Formulation A. Data is plotted as means with error bars (standard error).
Figure 7:
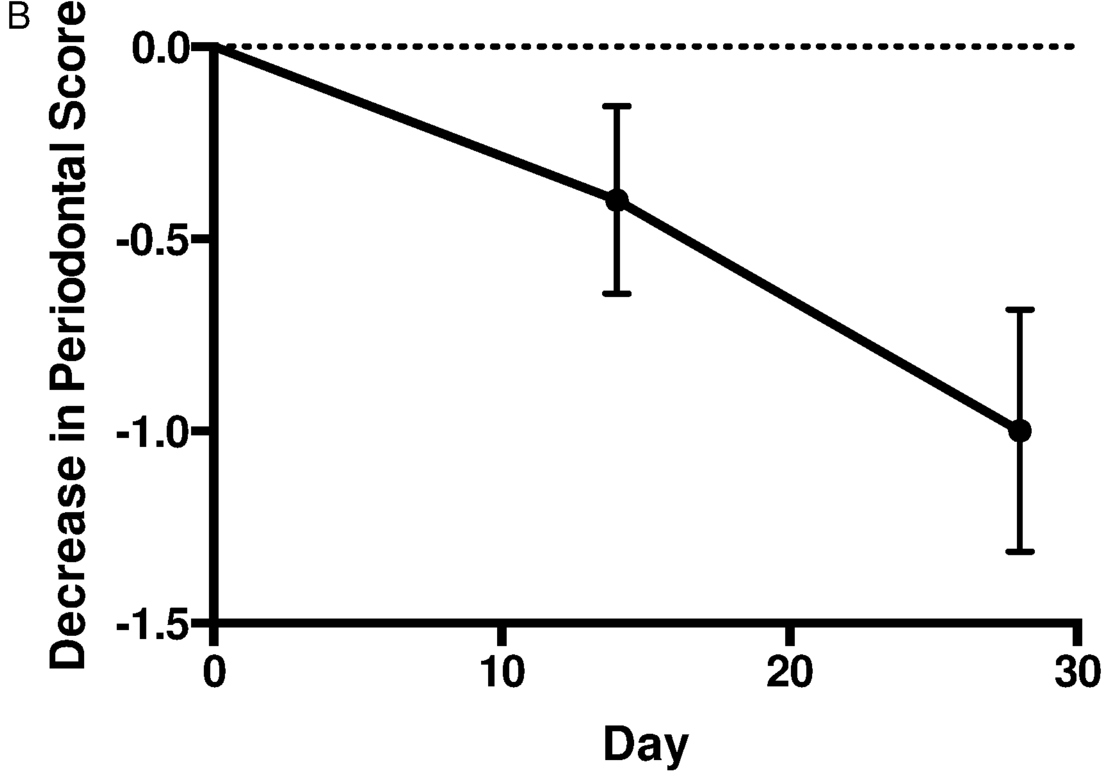
Figure 8:
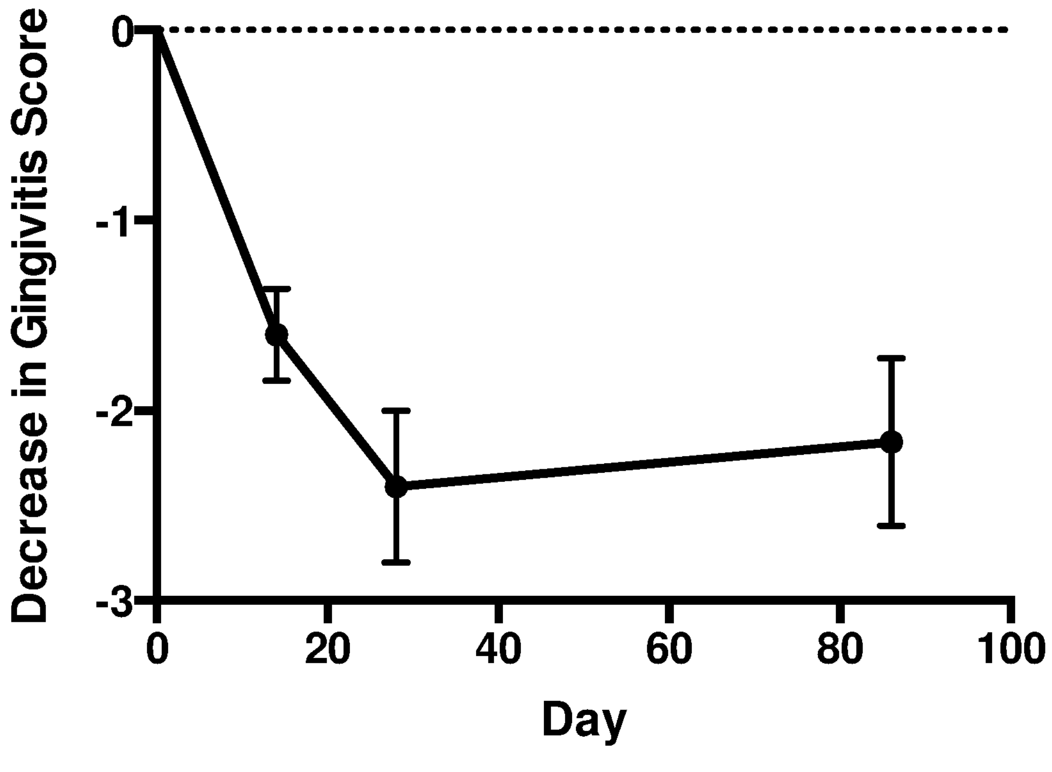
FIG. 8. There was a prolonged positive effect displayed in the dogs treated with Formulation A. The gingivitis status testing was continued also after the study ended, and the score continued to stay low even more than 60 days post-initiation. This effect appeared to persist for more than 60 days, suggesting that the non-healthy microbiota had been replaced by a healthier microbiota.

At day 28 of the treatment period, the OraStrip® test shows the level of gingivitis had decreased for the group treated with Formulation A, indicating a decreased risk of a more severe periodontal disease (FIG. 7A). The periodontal score had also decreased for the dogs treated with Formulation A, suggesting an improved dental health among the treated dogs (FIG. 7B). The level of gingivitis was also tested after the treatment period ended, and the score continued to stay low even more than 60 days after treatment stop (FIG. 8).

Conclusion

Formulation A appears to increase the dental health of the dogs, with decreased gingivitis and periodontal score. Furthermore, this effect appears to persist for more than 60 days. This suggests that the non-healthy microbiota has been replaced by a healthier microbiota.

REFERENCES

Asadi, Arezoo, et al. "A review on anti-adhesion therapies of bacterial diseases." *Infection* 47.1 (2019): 13-23.

Bryers, James D. "Medical biofilms." *Biotechnology and bioengineering* 100.1 (2008): 1-18.

Buckland, Emma L., et al. "Characterisation of antimicrobial usage in cats and dogs attending Uk primary care companion animal veterinary practices." *The Veterinary record* 179.19 (2016): 489-489.

Craik C S, Page M J, Madison E L. Proteases as therapeutics. Biochem J. 2011; 435:1-16.

Gilbert P, Das J, Foley I. Biofilm susceptibility to antimicrobials. *Adv Dent Res.* 1997; 11(1):160-7.

Meena, Himani, Asad Syed, and Busi Siddhardha. "A Review on Microbial Pathogenesis and Host Response." *Model Organisms for Microbial Pathogenesis, Biofilm Formation and Antimicrobial Drug Discovery*. Springer, Singapore, 2020. 47-60. WHO. New Report Calls for Urgent Action to Avert Antimicrobial Resitance Crisis. 2019.

Rosenthal, Mariana, et al. "Skin microbiota: microbial community structure and its potential association with health and disease." *Infection, Genetics and Evolution* 11.5 (2011): 839-848

Schommer, Nina N., and Richard L. Gallo. "Structure and function of the human skin microbiome." *Trends in microbiology* 21.12 (2013): 660-668.

Shaw, Liam P., et al. "Modelling microbiome recovery after antibiotics using a stability landscape framework." The ISME journal 13.7 (2019): 1845-1856.

The invention claimed is:

1. A composition comprising:

i. 0.02 to 0.09% w/w trypsin;

ii. 50 to 62% w/w glycerol;

iii. 0.002 to 0.04% w/w hyaluronic acid; and iv. 0.01 to 0.2% w/w salt comprising a divalent calcium ion.

2. The composition according to claim 1, wherein the composition further comprises:

a. 0.1 to 0.4% w/w buffer;

b. a monosaccharide or a monosaccharide derivative;

c. collagen; and/or d. water.

3. The composition according to claim 1, wherein the composition comprises or consists essentially of:

i. 0.02 to 0.09% w/w trypsin;

ii. 50 to 62% w/w glycerol;

iii. 0.002 to 0.04% w/w hyaluronic acid;

iv. 0.01 to 0.1% w/w calcium dichloride;

v. 0.1 to 0.4% w/w Tris or MOPS;

vi. 0.0 to 0.2% w/w mannose; and vii. 0.0 to 0.3% w/w collagen.

4. The composition according to claim 1, wherein the composition comprises or consists essentially of:

i. 0.04% w/w trypsin;

ii. 60% w/w glycerol;

iii. 0.02 to 0.04% w/w hyaluronic acid;

iv. 0.01% w/w calcium dichloride; and v. 0.1% w/w Tris or MOPS.

5. The composition according to claim 1, wherein a pH of the composition is between 6.0 to 7.5.

6. The composition according to claim 1, wherein the composition is in the form of a spray, a gel, a cream, lotion, an ointment, a foam, or a dental chew.

7. A method of treating a condition in a subject, wherein said condition is selected from the group consisting of microbial infections, dermatological conditions and oral conditions, said method comprising administering the composition according to claim 1 to said subject.

8. The method according to claim 7, wherein:

a. the microbial infection is selected from the group consisting of bacterial infections, fungal infections, yeast infections and viral infections, b. the dermatological condition is a skin infection or an inflammatory skin disease, or c. the oral condition is an oral infection or a dental infection.

9. The method according to claim 8, wherein the inflammatory skin disease is selected from the group consisting of atopic dermatitis, psoriasis, rosacea and acne.

10. The method according to claim 7, wherein the subject is a mammal.

11. The method according to claim 10, wherein the mammal is a dog, cat, horse or a human.

12. The method according to claim 7, wherein the composition is in the form of a spray, a gel, a cream, lotion, an ointment, a foam, or a dental chew.

13. The method according to claim 7, wherein the administration is topical administration.

14. A method for prevention and/or reduction of biofilm formation, wherein the method comprises administration of a composition according to claim 1.

15. The method according to claim 14, wherein the biofilm is a biofilm in or on a mammal.

16. The method according to claim 15, wherein the mammal is a dog, cat, horse or a human.

17. The method according to claim 14, wherein the biofilm is a biofilm of a biological surface.

18. The composition according to claim 1, wherein the composition consists of:

i. 0.02 to 0.09% w/w trypsin;

ii. 50 to 62% w/w glycerol;

iii. 0.002 to 0.04% w/w hyaluronic acid;

iv. 0.01 to 0.2% w/w calcium dichloride;

v. 0.1 to 0.4% w/w buffer; and vi. water.

19. The composition according to claim 1, wherein the composition consists of:

i. 0.04 to 0.09% w/w trypsin;

ii. 50 to 62% w/w glycerol;

iii. 0.002 to 0.02% w/w hyaluronic acid;

iv. 0.01% w/w calcium dichloride;

v. 0.1 to 0.4% w/w buffer; and vi. water.

20. The composition according to claim 1, wherein the composition consists of:

i. 0.04% w/w trypsin;

ii. 60% w/w glycerol;

iii. 0.002 to 0.02% w/w hyaluronic acid;

iv. 0.01% w/w calcium dichloride;

v. 0.1% w/w buffer; and vi. water.

* * * * *